United States Patent [19]
Kritzler

[11] Patent Number: 6,146,651
[45] Date of Patent: *Nov. 14, 2000

[54] NON-WOVEN FABRIC TREATED WITH A BIOCIDAL COMPOSITION AND A METHOD OF IMPREGNATING FABRIC TO PREVENT ROT

[75] Inventor: Steven Kritzler, Cronulla, Australia

[73] Assignee: Novapharm Research (Australia) Pty Limited, New South Wales, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/954,627

[22] Filed: Oct. 20, 1997

[30] Foreign Application Priority Data

Apr. 24, 1995 [AU] Australia ................... PN2625

[51] Int. Cl.$^7$ .................................... A01N 25/34
[52] U.S. Cl. .................. 424/404; 424/405; 424/411; 514/731
[58] Field of Search ..................... 424/402, 404, 424/405, 407, 411–415; 514/734–738; 2/901

[56] References Cited

U.S. PATENT DOCUMENTS

| | | | |
|---|---|---|---|
| 3,832,459 | 8/1974 | Berkeley | 424/45 |
| 5,288,486 | 2/1994 | White | 424/78.08 |
| 5,420,197 | 5/1995 | Lorenz et al. | 525/54.3 |
| 5,746,814 | 5/1998 | Malhotra et. al. | 106/18 |
| 5,786,615 | 6/1998 | Narayanan | 424/405 |

FOREIGN PATENT DOCUMENTS

WO 86/05391  9/1986  WIPO ............... A61K 9/08

OTHER PUBLICATIONS

Lioy–JP54098343 8179

*Primary Examiner*—Neil S. Levy
*Attorney, Agent, or Firm*—Venable; Ashley J. Wells

[57] ABSTRACT

A non-woven fabric treated with a biocidal composition including at least one halogenated phenolic biocide; a water soluble, film forming polymer which is a polyvinylpyrrolidone polymer or copolymer; and at least one surfactant, wherein a complex is formed between the halogenated phenolic biocide and the polyvinylpyrrolidone polymer or copolymer so that, after treatment of the non-woven fabric therewith and drying, no cloudy residue remains on the non-woven fabric. A method of impregnating a fabric to prevent rot includes contacting a non-woven fabric with a liquid biocidal composition containing at least one halogenated phenolic biocide, a water soluble, film forming polymer, which is a polyvinylpyrrolidone polymer or copolymer; and at least one surfactant, wherein a complex is formed between the halogenated phenolic biocide and the polyvinylpyrrolidone polymer or copolymer so that, after contacting the non-woven fabric with the liquid biocidal composition and drying, no cloudy residue remains on the non-woven fabric.

6 Claims, No Drawings

NON-WOVEN FABRIC TREATED WITH A BIOCIDAL COMPOSITION AND A METHOD OF IMPREGNATING FABRIC TO PREVENT ROT

FIELD OF THE INVENTION

The present invention relates to a biocidal preparation, in particular to a biocidal film preparation. The invention has been developed primarily for use as a surface disinfectant cleaner and impregnation agent and will be described hereinafter with reference to these applications. However, it will be appreciated that the invention is not limited to this particular field of use.

BACKGROUND OF THE INVENTION

Biocides are chemical compositions that are widely used in industry for disinfection and to prevent microbiological contamination and deterioration of commercial products, materials and systems. Of the biocides presently available, phenolic biocides are widely used.

In general, phenolic biocides are colorless and have minimal toxicological effects to humans i.e., cause little or no irritation to the skin. Although most phenolics have a characteristic odor, some of them, such as phenylphenols and dichlorophenes, have little odor and others, such as triclosan, have none. These properties are desirable as they enable such biocides to be used as an ingredient in orally administered pharmaceutical preparations; as an approved biocide for use in food establishments and plants; and in packaging material.

Phenolic biocides also have other desirable properties including a wide biocidal spectrum against microorganisms, such as bacteria and fungi; residual bacteriostatic properties; and, unlike other biocides, are not readily deactivated by organic matter, such as blood, serum and milk. These biocides therefore have a wide application as disinfectants and antimold products in general household, industrial, and other areas requiring disinfection, as they can be used in the destruction of the microorganisms present or the prevention of their further proliferation to numbers that would be significantly destructive to the substrate or system being protected.

An example of a phenolic biocide is dichlorophene which, in addition to its antibacterial properties, is particularly effective against fungi, such as yeast mold and mildew. This property enables such derivatives to be used mainly as a preservative against mildew and rot in a variety of products including paper and textiles.

Another example of a phenolic biocide used is trichloro hydroxy diphenyl ether (Triclosan) which is an effective ingredient in deodorant and in skin cleansing preparations.

Hitherto, phenols have been used in industrial cleaners in an aqueous solution at very high pH (above pH 11). The use of cleaners with such high pH is undesirable in households. In order to overcome this problem, phenols have been used in alcoholic solution but such use leaves visable surface residues and is disadvantageous for household use.

To obtain aqueous detergent solutions of phenolic biocides they have first to be converted into their water soluble alkali salts, usually with sodium hydroxide, resulting in alkaline solutions of a pH of at least 11.0. The high alkalinity of these solutions excludes them from application in households and on surfaces susceptible to deterioration by alkalis. Their use has therefore been restricted to industrial cleaners for stainless steel equipment and hard floor surfaces in food processing and glass bottle washing plants and other industrial plants and areas where the higher alkalinity is acceptable.

When dissolved in an alcoholic-aqueous mixture with the addition of a small amount of a suitable surfactant to form a disinfectant cleaning preparation, such a solution will on drying leave streaks and partly greyish areas on treated surfaces due to the remaining insoluble residues of the biocide.

Triclosan which finds its main application in antiseptic skin and hand cleansing preparations has been either used in suspension, or solubilized with non-ionic surfactants with resultant loss in activity.

In mildew and rot proofing of paper and textiles phenylphenol and especially dichlorophene are widely used as their sodium salt solution for the impregnation of these materials against fungal infection and prevention of mold formulations.

The high alkalinity of these solutions causes weakening of the strength of fibers and loss of the biocides either by leaching out in moist climates or by lack of binding to the surfaces treated. This has been prevented in the past by neutralization of the alkali salt and/or bonding the biocides by means of a metal salt, such as zirconium acetate. These processes necessitate a further manufacturing procedure, use of additional equipment and additional cost for the neutralization agent. These additional measures are required as bonding the biocidal agent onto the material to be protected was not always effective, especially when prolonged periods of protection were required.

OBJECT OF THE INVENTION

It is therefore an object of the invention to ameliorate at least some of the above disadvantages.

Preferred embodiments of the invention overcome the above disadvantages by providing a liquid biocidal preparation for the disinfection of solid surfaces and impregnation of paper, textiles and non-woven fabrics which at the same time protects them against reinfection by microorganisms.

DISCLOSURE OF THE INVENTION

According to a first aspect, the present invention consists in a biocidal preparation comprising a halogenated phenolic biocide and less than 8 wt % of a polyvinylpyrrolidone polymer or copolymer dissolved in an aqueous alcoholic solvent, the combination drying on evaporation of the solvent to form a clear film.

For preference the biocide is selected from the group consisting of triclosan, dichlorophene, chlorophene, p-chloro-m-xylenol (PCMX), hexachlorophene, o-phenylphenol, pentachlorophenol (PCP) and bromophene.

Preparations according to the invention surprisingly provide a substantially aqueous solution of a biocide preparation which, in the pH range of 2–10.0, on drying form clear films with disinfecting properties on the treated surface (which can be organic or nonorganic) and provides good adherence. The inventors believe that a colorless complex is formed between the polymer (or copolymer) and the selected phenolic biocide which surprisingly results in a desirably clear film.

If desired, a rot proofing solution can be added during the manufacturing process to the pulp of paper or textile fibers prior to sheeting and drying. It has been found that in this use preparations according to the invention provide excellent binding to the substrate with slow release of the biocide and without interfering with the feel or "handle" of the textile.

According to a second aspect, the present invention consists in a general household cleaner comprising:

0.1–3% by weight of dichlorophene or a combination of dichlorophene with o-phenylphenol, and less than 8% by weight of a polyvinylpyrrolidone polymer or copolymer in an aqueous alcoholic solvent.

According to a third aspect, the present invention consists in a medical cleaner comprising:

0.1–5.0% by weight of triclosan, and less than 8% by weight of a polyvinylpyrrolidone polymer or copolymer thereof, in an aqueous alcoholic solvent.

According to a fourth aspect, the present invention consists in a process of preparing a biocidal composition comprising the steps of combining a phenolic biocide selected from triclosan, dichlorophene, chlorophene, p-chloro-m-xylenol (PCMX), hexachlorophene, o-phenylphenol, pentachlorophenol and/or bromophene, with less than 8 wt %, based on the total weight of the composition, of a polyvinylpyrrolidone or copolymer in an aqueous alcoholic solvent.

The biocidal solutions are best prepared by prior dissolving the biocide and the polymer in alcohol(s) with subsequent addition of water not exceeding the amount which would cause turbidity and separation of the biocide.

Desirably, an effective amount of at least one anionic or non-ionic surfactant or a combination of both is included in the preparation.

According to a fifth aspect, the invention consists in a non-woven fabric wherein the binder includes at least one phenolic biocide, a water soluble film forming polymer, and at least one surfactant.

According to a sixth aspect, the present invention consists in a method of impregnating a fabric to prevent rot comprising contacting a non-woven fabric with a biocidal preparation containing at least one phenolic biocide, a water soluble film forming polymer, and at least one surfactant.

PREFERRED EMBODIMENTS OF THE INVENTION

The film forming polymers preferably used in the present invention are polymers in which the biocide is soluble, and are usually selected based on their intended application. Polyvinylpyrrolidone (PVP) and its copolymers with vinylacetate aminoacrylates and trimethylammonium chloride are a preferred choice for disinfecting surface cleaners with residual biocidal activity and polyvinyl-maleic copolymers for impregnation of paper and textile materials. More preferably for disinfecting and cleaning, polyvinylpyrrolidones with a degree of polymerization (K value) of 15, 30, 60 and 90 (most preferably a polyvinylpyrrolidone with a degree of polymerization of 90) or copolymers with vinylacetate comprising from 20 to 80% polyvinylpyrrolidone, (most preferably comprising at least 50% vinylacetate and possessing cationic character) are used. Another suitable polymer for disinfecting/cleaning is QAFQUAT-HS made by ISP Corporation, USA.

For impregnation, the amount of polymer used is preferably in the range of from 0.01 parts of the polymer to 99.9 parts of polymer for each 1 part of phenolic biocide. More preferably the polymer is in the range of from 0.01 to 50 parts and most preferably from 0.01 to 1 part for each part of phenolic biocide. For disinfecting/cleaning, the amount of polymer used is preferably less than 8 wt %, most preferably less than 2 wt % based on the weight of the composition.

Preferably, the phenolic biocides are selected from the group consisting of pentachlorophenol (PCP); p-chloro-m-xylenol (PCMX); hexachlorophene; o-phenylphenol; dichlorophene; chlorophene; bromophene; Triclosan or a combination of these biocides.

For general household cleaners and for disinfecting food preparation surfaces phenolic biocides dichlorophene or a combination of dichlorophene with o-phenylphenol are recommended. The concentration of the phenolic biocides in solution is preferably in the range of from 0.2–1.0% and more preferably from 0.2–0.5% by weight of the composition.

For medical professional premises the preferred biocide is triclosan used at a concentration preferably in the range of from 0.1–3.0%, and more preferably from 1.0–2.0% by weight of the composition. The biocidal preparation can be used for disinfecting medical instruments such as endoscopes.

The concentration of the biocides used for the impregnation of paper and textiles is often dependent on the method of preparation. Preferably, the amount of uptake is between 0.05 to 1.0% based on the weight of the material. More preferably the range is between 0.1 to 0.5% by weight of the material.

Where a surface disinfectant cleaner is required a certain amount of a detergent should be included in the preparation. The detergent is preferably selected from the range of anionic surfactants, although other surfactants can also be used on their own or in combination with an anionic surfactant. It is also advantageous to include a small amount of a surfactant in an impregnation solution to ensure uniform wetting of the treated material.

Suitable anionic surfactants include sodium salts of dodecylbenzenesulphonate and laurylether sulphate; phosphate esters of nonylphenolethoxylates; nonylphenoxyphosphoric acid esters or a combination of these surfactants. A preferred surfactant is the sodium salt of dodecylbenzenesulphonate which can be used on its own or in combination with another anionic surfactant.

An effective amount of surfactant will depend on the intended application of the final product. That is, a disinfectant surface cleaner product will have a relatively high proportion of surfactant to ensure it has good cleaning properties. On the other hand for impregnation of paper and textile materials the content of the surfactant will be much lower as their purpose is only in wetting the surfaces of the paper and textile fibers and assuring better penetration.

Suitable alcohols, include any water soluble lower alkyl alcohols such as methanol and ethanol, but higher alkyl alcohols, such as iso- and n-propanol, may be used on their own or in combination with lower alcohols preferably in an amount not exceeding 30% weight by volume in disinfectant cleaner and impregnation liquid.

It is advantageous, where a higher degree of disinfection is desired, to include one or more aromatic alcohols, such as benzyl-, phenoxy-and dichlorobenzylalcohol generally in an amount of not more than 2.0% by weight.

The invention will now be more particularly described by way of example only with reference to the following examples:

EXAMPLE 1

| Biocidal Surface Cleaner | Domestic |
|---|---|
| Dichlorophene | 0.3 Kg. |
| Gardinol* 25L | 5.0 Kg. |
| Anthrox C0630** | 0.5 Kg. |
| PVP | 0.75 Kg. |
| isopropanol | 25.00 L |
| water to make | 100.0 L |

*Sod. Dodecylbenzosulphonate ex Albright & Wilson
**Nonyl Phenol Ethoxylate ex Rhone-Poulenc

EXAMPLE 2

| Biocidal Surface Cleaner | Institutional (% by weight of composition) |
|---|---|
| Dichlorophene | 0.3 % |
| o-phenylphenol | 0.2 % |
| Luviskol VA60140* | 0.4 % |
| Gardinol 25L | 5.0 % |
| Rhodafac RE-610** | 0.5 % |
| isopropanol | 30.0 % |
| water to make | 100.0 parts by volume |

*Polyvinyl-vinylacetate polymer 60/40 ex-BASF Inc
**Rhone-Poulenc

EXAMPLE 3

| | (% by weight of composition) |
|---|---|
| Triclosan | 0.5% |
| Phenoxyethanol | 1.0% |
| Antaron P904* | 1.5% |
| Gardinol 25L | 5.0% |
| n-Propanol | 30.0% |
| Fragrance as desired | |
| water to make | |
| 100 parts by volume | |

*alkylated vinylpyrrolidone polymer ex-ISP Chemicals

EXAMPLE 4

Biocidal Bathroom and Tile Cleaner

| | |
|---|---|
| Sodium carboxy methyl cellulose | 0.35% |
| Dichlorophene | 0.50% |
| Ethanol (95%) | 5.00% |
| Isopropanol | 5.00% |
| Nansa SSA/S* | 4.00% |
| Teric N 10** | 2.00% |
| EDTA 4 Na | 0.10% |
| Tri-sodiumpolyphosphate | 1.00% |
| Sodium Hydroxide | adjust to pH 7.5–8.0 |
| Hydrogene Peroxide 35% | 12.00% |
| Water | q.s. to 100,00 |

*Sodium dodecyl benzene sulphonate, Albright & Wilson
**Nonyl phenolethoxylate ICI Chemicals

Impregnation Fluid

Formulations prepared for this purpose will depend on the type of material to be impregnated, the degree of rot proofing required and the type and conditions of application. The recommended phenolic biocide for that purpose is dichlorophene with a deposit of 0.1–0.7% by weight of the material for textiles and 0.05–0.5% by weight of the material for paper. Film forming polymers to be used would be a polyvinyl maleic polymer, such as Gantrez AN (GAF Inc.). The alcohol could be isopropyl and the concentration of the anionic surfactants would be sufficient to obtain satisfactory wetting of the surfaces to be treated. Due to possible excessive foaming in some formulations, a de-foaming agent(s) is sometimes added.

A typical formulation for the impregnation of a non-woven cloth would be:

| | |
|---|---|
| Dichlorophene | 12.0 kg |
| Gantrez AN 119* | 0.3 g |
| Empicol SQ770** | 2.75 g |
| Ven Gell B*** | 0.5 kg |
| Water to make | 30.0 kg |

*Sod. Laurylalkoxysulfate ex Albright & Wilson
**Polyvinyl maleic polymer ex GAF Inc
***Ex-Veegum Vanderbilt Co. Inc.

The components are mixed into a uniform slurry. The amount is incorporated into 200 kg of a standard binder—resulting in an active content of dichlorophene of about 5.0% by weight. At an average pick-up of the binder of 7 g/sq meter, the deposit of the biocide will be approximately 0.3% by weight.

The invention extends additionally to include a film formed from a preparation as described and to a method of treating a surface by application of a preparation as described.

Although the invention has been described with reference to specific examples, it will be appreciated by those skilled in the art that the invention may be embodied in many other forms.

What is claimed is:

1. A non-woven fabric treated with a biocidal composition, comprising:

at least one halogenated phenolic biocide; a water soluble, film forming polymer which is a polyvinylpyrrolidone polymer or copolymer; and at least one surfactant, wherein a complex is formed between the halogenated phenolic biocide and the Polyvinylpyrrolidone polymer or copolymer so that, after treatment of the non-woven fabric therewith and drying, no cloudy residue remains on the non-woven fabric.

2. The non-woven fabric according to claim 1, wherein the film forming polymer is one of polyvinylpyrrolidone or its copolymer with vinylacetate, or polyvinyl-maleic copolymer.

3. The non-woven fabric according to claim 1, wherein the at least one halogenated phenolic biocides is selected from the group consisting of pentachlorophenol (PCP), p-chloro-m-xylenol (PCMX), hexachlorophenel, o-phenylphenol, dichlorophene, chlorophene, bromophene, trilosan and a combination thereof.

4. A method of impregnating a fabric to prevent rot, comprising
contacting a non-woven fabric with a biocidal composition containing at least one halogenated phenolic biocide, a water soluble, film forming polymer, which is a polyvinylpyrrolidone polymer or copolymer; and at least one surfactant,
wherein a complex is formed between the halogenated phenolic biocide and the polyvinylpyrrolidone polymer or copolymer so that, after contacting the non-woven fabric with the liquid biocidal composition and drying, no cloudy residue remains on the non-woven fabric.

5. The method according to claim 4, wherein the polyvinylpyrrolidone polymer or copolymer is present in an amount which ranges from 0.01 to 99.9 parts of polyvinylpyrrolidone polymer or copolymer per 1 part of halogenated phenolic biocide.

6. The method according to claim 4, wherein the halogenated phenolic biocide is taken up by the non-woven fabric in an amount ranging between 0.05 and 1 % based on the weight of the fabric.

* * * * *